May 17, 1960 G. A. SPOOR Plant Pat. 1,942
ELEAGNUS PLANT
Filed Dec. 15, 1958
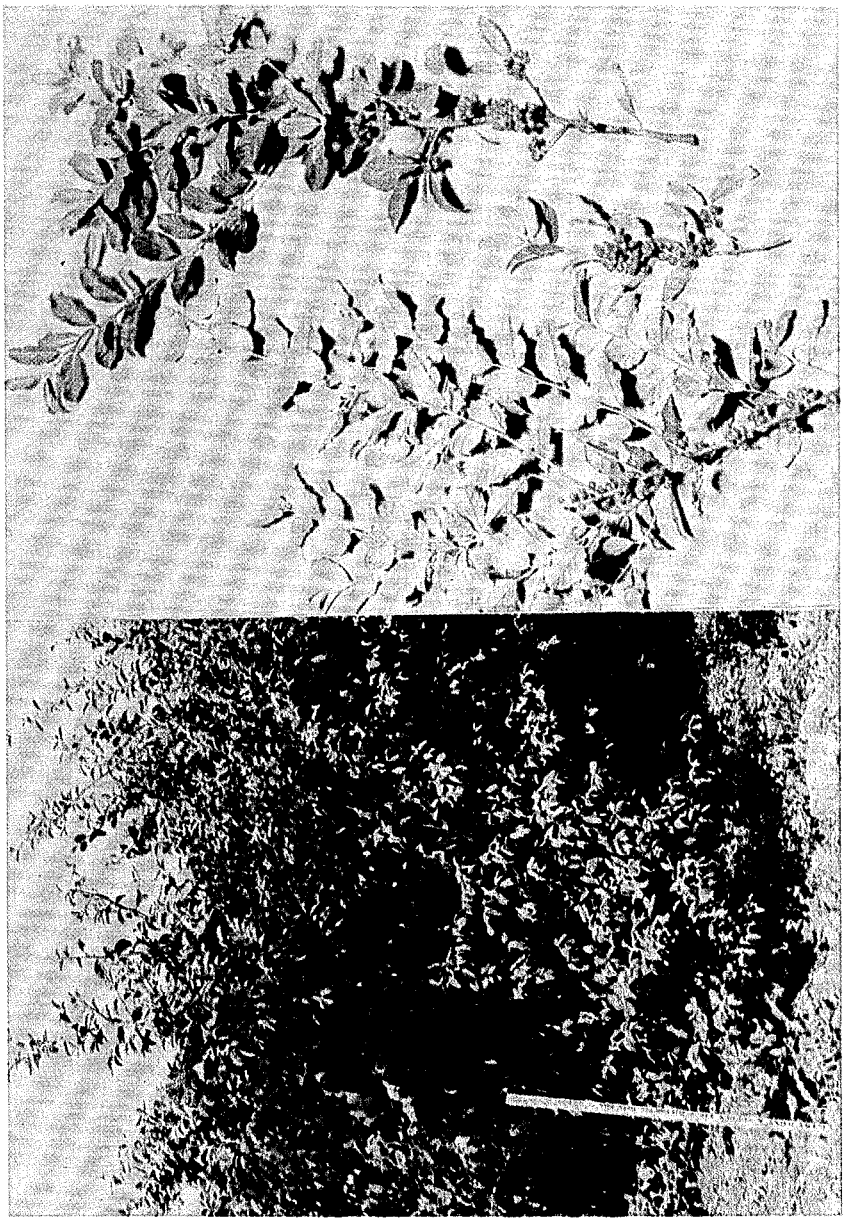
INVENTOR
Gerald A. Spoor
BY Robbins Robb
ATTORNEYS United States Patent Office Plant Pat. 1,942
Patented May 17, 1960

1,942

ELEAGNUS PLANT

Gerald A. Spoor, Tulsa, Okla.

Application December 15, 1958, Serial No. 780,647

1 Claim. (Cl. 47—59)

The present invention relates to a new and distinct variety of Eleagnus plant, which was discovered by me on my cultivated property at Tulsa, Oklahoma.

In the course of operating a nursery on my property, my attention was attracted by the silvery foliage of a small plant about 18 inches tall which was growing under the irrigation piping where good growing conditions prevail. Largely out of curiosity, I carefully preserved the plant and kept it under close observation. After a period of several years, it bore attractive red berries, which further increased my interest. While I concluded that the plant was an Eleagnus plant, it was definitely different from any variety with which I was familiar, such as "*Eleagnus angustifolia*" (unpatented), commonly known as "Russian olive," and "*Eleagnus fruitlandi*" (unpatented), a form of "*Eleagnus pungens*" (unpatented), both of which were well known in the Tulsa, Oklahoma area and had been at one time or another previously grown on my property, or were otherwise quite familiar to me as the result of plants being grown in the vicinity of my property.

Continued observations and asexual reproductions of the original plant, as made by me in my nursery at Tulsa, definitely established that the newly found variety was hardier in the winter and more drought and heat resistant in the summer than "*E. fruitlandi.*" My observations and tests demonstrated that the new variety grows easily in the Southwest and readily withstands the heat and droughts which prevail in that area.

In comparison with "Russian olive," my new variety is more compact in its habit of growth and not as tall; it has brighter foliage, larger leaves, and holds its leaves longer, but not as long as "*E. fruitlandi.*" It is almost evergreen, and contrary to "*E. fruitlandi,*" does not kill by frost in the Tulsa area when the winters are abnormally cold, although it does not bear berries when subjected to late frosts.

Prolonged observations of my new Eleagnus have conclusively demonstrated that it has three distinct seasons of ornamental value:

(1) In the spring, it bears inconspicuous, sweet-scented flowers;

(2) All summer it is clothed with brilliant silvery foliage; and (3) In the fall, it bears attractive red berries from September through November, and the berries do not begin to deteriorate until the temperature drops to about 25° F., but retains some color even at temperatures of 15° F.

Asexual reproduction of my new Eleagnus by cuttings, as performed by me on my property at Tulsa, Oklahoma, shows that the foregoing characteristics and distinctions come true to form and are established and transmitted through succeeding propagations.

The accompanying drawing shows a typical specimen plant of my new Eleagnus, as well as specimen branches with foliage and berries in different stages of development and on an enlarged scale, all as depicted in color as nearly true as it is reasonably possible to make the same in a color illustration of this character.

The following is a detailed description of my new Eleagnus, with color terminology in accordance with Koster's Color Guide, except where general color terms of ordinary dictionary significance are obvious;

*Plant*

(Observations made from specimens grown at Tulsa, Oklahoma.)

Growth: Vigorous; shrub form.
Root: Medium deep-rooted.
Leaves: Many.
*Size.*—Length—from about 1½ inches to about 2 inches. Width—from about 1 inch to about 1½ inches.
*Petiole.*—Short; about ¼ inch long; sturdy.
*Color.*—Upper side—Silvery Sage Green, Plate 78. Under side—Silvery Pearl Grey, Plate 100.
*Pubescence.*—Very scant.
*Groove.*—Slight.
Culture: Thrives in light, well-drained soil.
Disease and insect resistance: No diseases or insect damage observed over a prolonged period of observation at Tulsa, Oklahoma, except slight grasshopper damage.
Frost resistance: Good, but drops leaves, although does not kill, under abnormally cold weather conditions in the Tulsa, Oklahoma area.
Drought resistance: Very good.

*Bloom*

Blooming period: Blooms in same general period as peaches in same locality.
*Date of first bloom.*—About March 1st.
*Date of full bloom.*—About March 15th.
Flowers: Many; inconspicuous; borne in trusses like chokeberry.
*Color.*—Yellowish-white.
*Fragrance.*—Sweet-scented and agreeable.

*Fruit*

Fruiting stems: Short; from about ⅛ inch to about ¼ inch long; slender.
Size: Variable; small; about ¼ inch in diameter and fairly round when matured, but somewhat flattened at ends.
Form: Uniform; globose, with apex depressed.
Surface: Glossy. Color—near Oxblood Red, Plate 25, with numerous dots or speckles of Creamy White, Plate 2.
Flesh: Somewhat juicy.

I claim:

A new and distinct variety of Eleagnus plant, substantially as herein shown and described, characterized particularly as to novelty by the unique combination of compact and almost evergreen habits of growth, good winter hardiness and drought and heat resistance, with consequent ease of growth and adaptability to the Southwest geographical area of the United States, relatively large and brilliant silvery foliage throughout the summer season, with prolonged retention of the leaves, and a habit of bearing inconspicuous, sweet-scented flowers in the spring and attractive red berries in the fall, said berries being capable of withstanding low temperatures down to about 25° F. before deteriorating, still showing some color down to about 15° F.

No references cited.